United States Patent [19]

Pratt

[11] 4,249,541
[45] Feb. 10, 1981

[54] BIOPSY DEVICE

[75] Inventor: David S. Pratt, 80 Susquehanna Ave., Cooperstown, N.Y. 13326

[73] Assignee: David S. Pratt, Cooperstown, N.Y.

[21] Appl. No.: 33,742

[22] Filed: Apr. 26, 1979

[51] Int. Cl.³ .............................................. A61B 10/00
[52] U.S. Cl. ................................ 128/753; 128/214.4; 128/768
[58] Field of Search ...................... 128/214.4, 749, 753, 128/763, 768

[56] References Cited

U.S. PATENT DOCUMENTS

| | | | |
|---|---|---|---|
| 3,438,373 | 4/1969 | Pannier, Jr. | 128/214.4 |
| 3,500,828 | 3/1970 | Podhora | 128/214.4 |
| 3,537,451 | 11/1970 | Beck et al. | 128/214.4 |
| 3,993,079 | 11/1976 | Gatztañondo | 128/347 |
| 4,006,744 | 2/1977 | Steer | 128/214.4 |
| 4,052,989 | 10/1977 | Kline | 128/349 R |
| 4,073,297 | 2/1978 | Kopp | 128/214.4 |
| 4,096,860 | 6/1978 | McLaughlin | 128/214.4 |

OTHER PUBLICATIONS

Wang, K. O., et al., *Amer. Rev. of Respiratory Disease*, vol. 118, 1978, pp. 17–21.

*Primary Examiner*—Kyle L. Howell
*Attorney, Agent, or Firm*—Gregory A. Madera

[57] ABSTRACT

A biopsy unit comprising an outer catheter, and an inner aspirator, the catheter including a longitudinally extending hollow flexible housing tube and means for gripping the aspirator, the aspirator including a longitudinally extending hollow flexible aspirating tube adapted to slide longitudinally within the housing tube when not gripped by the gripping means, a connector adapted to be fitted to a suction source and fastened to one end of the aspirating tube, and a hollow needle fastened to the other end of the aspirating tube, the lumen of the needle communicating with the connector through the aspirating tube.

16 Claims, 9 Drawing Figures

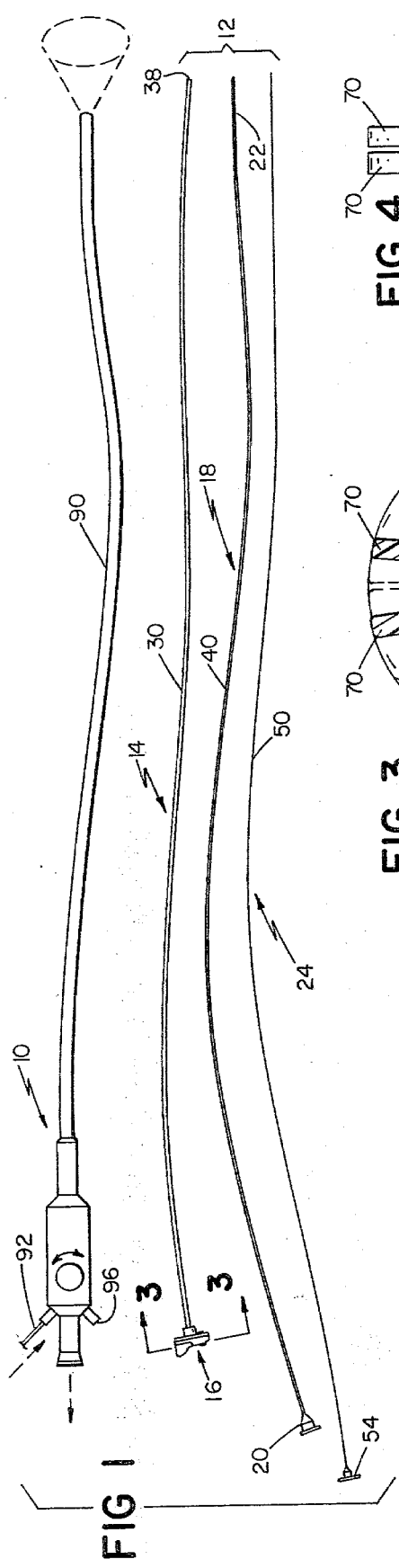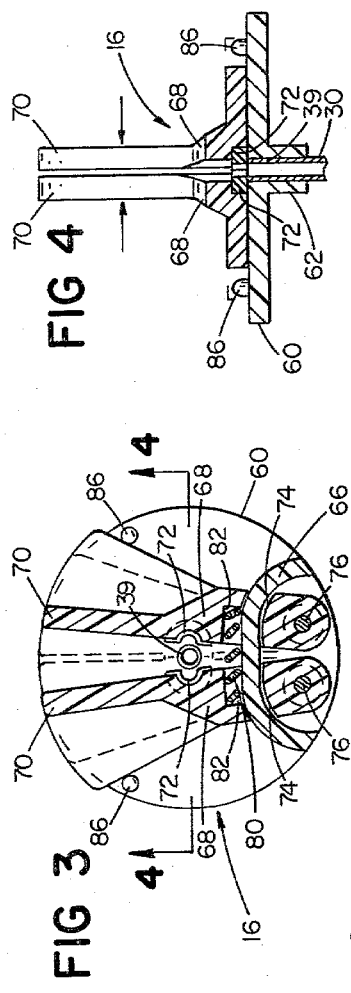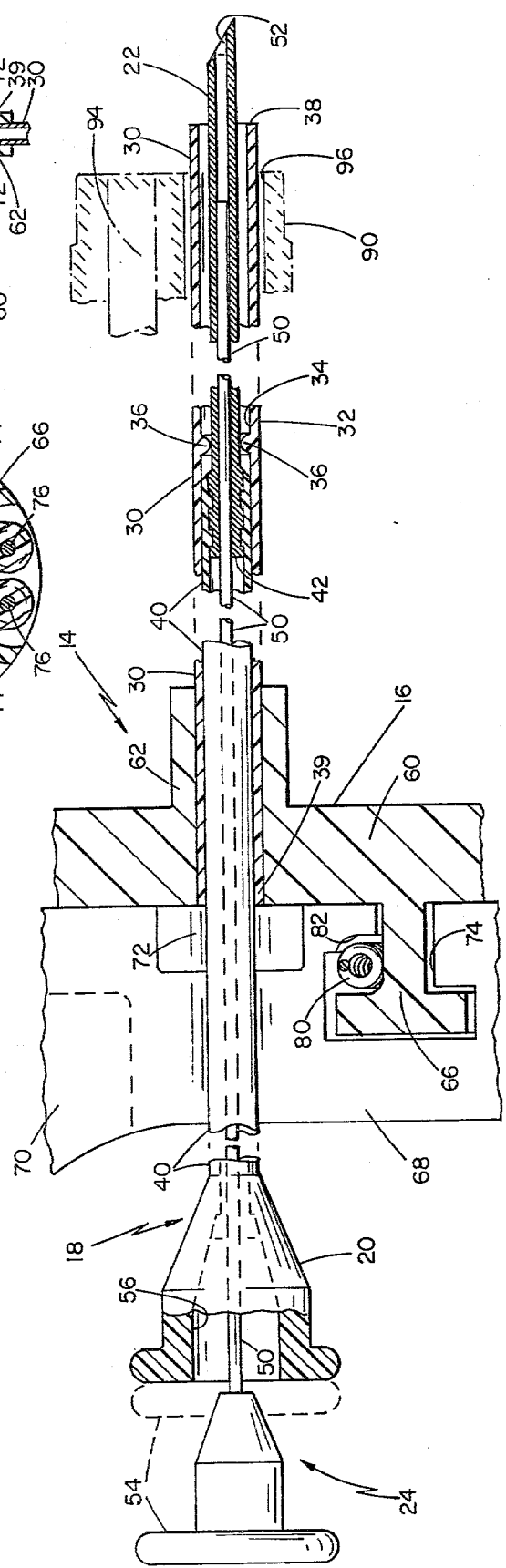

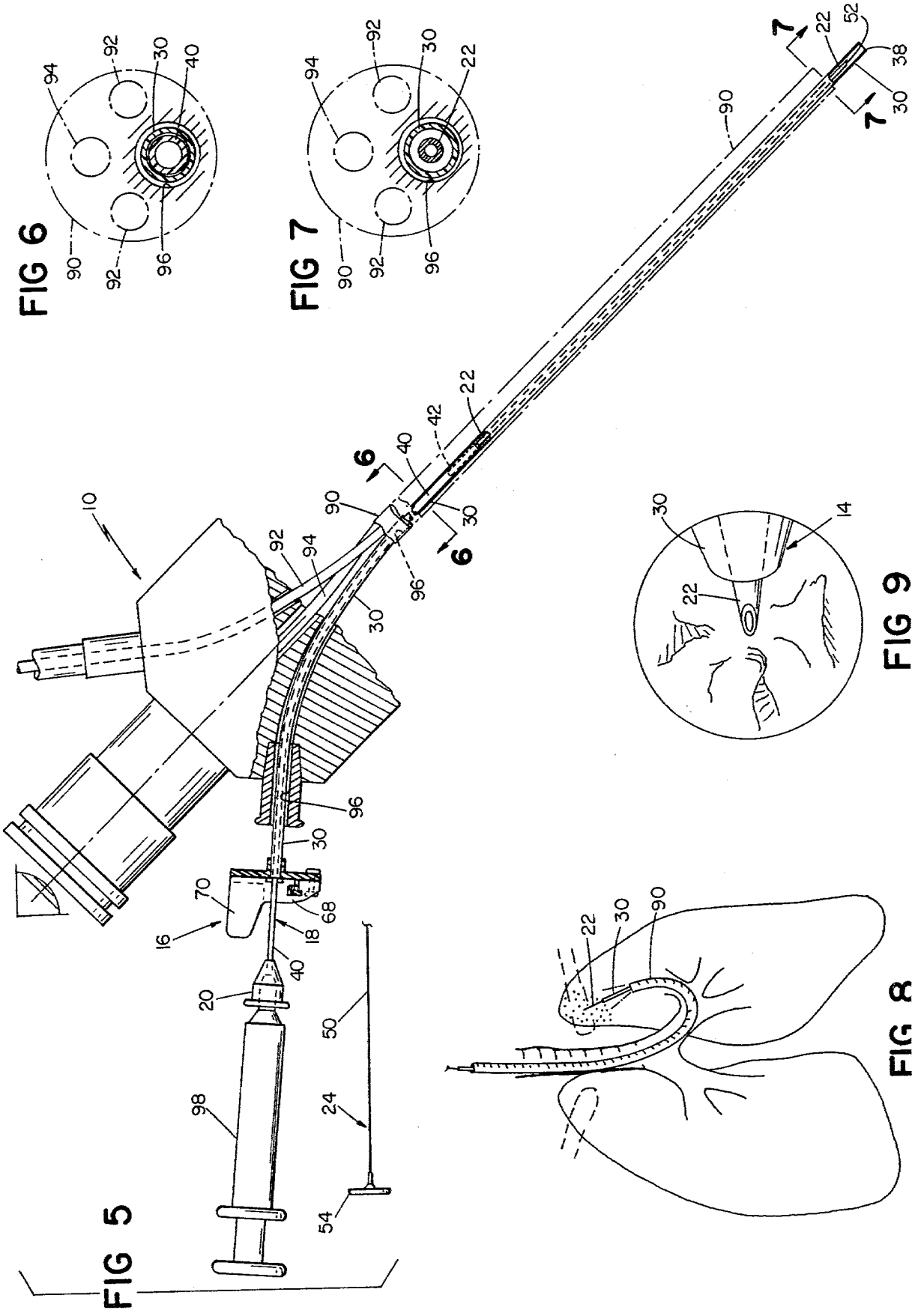

BIOPSY DEVICE

FIELD OF THE INVENTION

This invention relates to devices for obtaining cell samples from patients for cytologic examination, and in particular to a device for obtaining cell samples from the lung.

BACKGROUND OF THE INVENTION

It is often necessary for a physician to sample the cellular contents of a patient's lung to determine the nature of an observed abnormality. Cell samples from lesions on the periphery of the lung may sometimes be obtained by direct lung puncture, wherein a needle is driven through the chest wall. This technique is not only painful, but also may result in lung collapse. Lesions near the center of the lung require more invasive diagnostic procedures, such as the conventional thoracotomy, a surgical incision of the chest wall. Thoracotomies are dangerous and can only be considered for use with patients healthy enough to survive the trauma of major surgery.

In Wang et al., "Bronchoscopic Needle Aspiration Biopsy of Paratracheal Tumors", Volume 118, *American Review of Respiratory Disease*, 1978, a transtracheal needle aspiration technique is described, wherein a stiff esophageal varices needle is inserted into the lung through the lumen of a rigid bronchoscope. This is a relatively noninvasive technique, but it has substantial limitations. There is a great deal of patient discomfort associated with rigid bronchoscopy, and it is often not possible to manuever the rigid bronchoscope for access to the more distal regions of the lung.

Biopsies have also been made with a flexible fiber optic bronchoscope, conventionally used to visually inspect the lungs. Such bronchoscopes include a small diameter flexible viewing tube, which allows the physician to enter the airways of the lungs through the larynx. The tube is usually advanced through the nose and down the windpipe, with a minimum of discomfort to the patient. Conventionally, tissue is sampled by means of a small spoon-shaped forceps which is passed through a hollow aspirating channel in the viewing tube. The small size and opening range of the forceps limit the amount of tissue that can be retrieved, with a resulting reduction in capability of obtaining adequate specimens for cytologic examination. Also, forceps are unable to reach mass lesions under the lining of the airways, or lesions far out on the edge of the lung. Further, the biting and ripping action of the jaws of the forceps is not conductive to obtaining clean specimens with minimal chance of bleeding.

SUMMARY OF THE INVENTION

The invention provides a biopsy unit that can be used with conventional flexible fiber optic bronchoscopes to obtain cell samples with little discomfort to the patient and with minimal chance of inducing bleeding or pneumothorax. The unit enables guided, accurate biopsy of smooth submucosal masses, lesions located at distal portions of the lungs, and other tumors heretofore sampled only with great difficulty and at substantial risk to the patient.

The invention features a biopsy unit comprising an outer catheter, and an inner aspirator, the catheter including a longitudinally extending hollow flexible housing tube and means for gripping the aspirator, the aspirator including a longitudinally extending hollow flexible aspirating tube adapted to slide longitudinally within the housing tube when not gripped by said gripping means, a connector adapted to be fitted to a suction source and fastened to one end of the aspirating tube, and a hollow needle fastened to the other end of the aspirating tube, the lumen of the needle communicating with the connector through the aspirating tube. In preferred embodiments the unit includes an obturator having a longitudinally extending wire adapted to slidingly fit within the aspirating tube and the lumen of the needle, and a head attached to the wire and adapted to fit within the connector when the wire is inserted in the aspirator; the gripping means comprises a disc fastened to the proximal end of the housing tube having an integral guide rib, and levers pivotally mounted to the disc and having cooperating grooves for movement along the rib guide, the levers being adapted to clamp the aspirating tube; the aspirating tube is cylindrical and the levers are provided with semicircular bushings adapted to grip the periphery of the catheter without crushing it; the levers have opposed notches forming a cavity, and a spring positioned in the cavity biases the levers away from each other; the disc has stops to limit the movement of the levers under the biasing force of the spring; the housing tube and aspirating tube are polyethylene; the walls of the housing tube are coated with Teflon; the housing tube has an outside diameter no greater than 1.5 mm; the needle is a stainless steel needle no greater than 22 gauge; the connecter is adapted to be fitted to a syringe or a manometer; and the housing tube has an integral stop to limit the longitudinal movement of the needle of the aspirator.

DESCRIPTION OF THE PREFERRED EMBODIMENT

The structure and operation of the preferred embodiment are as follows.

DRAWINGS

FIG. 1 is a reduced side elevation, somewhat schematic, of a conventional fiber optic bronchoscope and a disassembled aspirating unit embodying the invention.

FIG. 2 is an enlarged side elevation, partially in section and broken away, showing the assembled aspirating unit of FIG. 1 inserted in the bronchoscope.

FIG. 3 is a section through 3—3 of FIG. 1.

FIG. 4 is a section through 4—4 of FIG. 3.

FIG. 5 is a somewhat schematic side elevation, partially in section and broken away, showing the aspirating unit of FIG. 1 inserted in the bronchoscope for use.

FIG. 6 is a section through 6—6 of FIG. 5.

FIG. 7 is a section through 7—7 of FIG. 5.

FIG. 8 is a somewhat schematic view of the aspirating unit of FIG. 1 in use, with the bronchoscope being inserted in the lung of a patient.

FIG. 9 is a somewhat schematic view of an image transmitted through the bronchoscope to the operator of the aspirating unit while in use as in FIG. 8.

STRUCTURE

There is shown in FIG. 1 a conventional fiber optic bronchoscope 10, and a transbronchial aspirating needle catheter unit 12, including an outer or guiding catheter 14 having a clamp 16, an inner aspirator 18 having a syringe adapter 20 and a needle 22, and an obturator 24.

Turning now to FIG. 2, housing tube 30 of outer catheter 14 is extruded polyethylene (140 cm long, 1.5 mm O.D., 1.3 mm I.D.). The outer and inner walls 32, 34 of tube 30 are coated with Dupont Teflon polytetrafluoroethylene. Extrusion of tube 30 is interrupted to provide an integral needle guide 36, located 8 cm from tip 38 of tube 30. Clamp 16 is bonded by epoxy resin and heat to end 39 of tube 30.

Aspirating tube 40 of inner aspirator 18 is extruded polyethylene (155 cm long, 1.2 mm O.D., 1.0 mm I.D.). Polyvinyl chloride syringe adapter 20 and the hub or neck 42 (1.0 mm O.D.) of flexible stainless steel needle 22 (22 gauge, 12 cm long) are bonded by epoxy resin, pressure and heat to tube 40.

Obturator 24 has a stainless steel wire body 50, adapted to slidingly fit within the lumen 52 of needle 22. Wire 50 is attached by epoxy resin and heat to polyvinyl chloride head 54, which is shaped to fit within cavity 56 of adapter 20. Wire 50 extends to the end of needle 22 when obturator 24 is completely inserted in aspirator 18 (as shown in broken lines in FIG. 2).

Turning now to FIGS. 3 and 4, clamp 16 includes a polyvinyl chloride disc 60 attached to the proximal end of tube 30 by a central neck portion 62 and having an integral guide rib 66, and levers 68 having finger grips 70 and semicircular nylon bushings 72. Each of the levers 68 has a cooperating groove 74 (see also FIG. 2) and is pivotally mounted to disc 62 by a stainless steel rivet 76 for movement along guide 66. Spring 80, mounted in the cavity formed by notches 82 in levers 68, biases the levers outwardly to a fully opened position, defined by stops 86.

OPERATION

Turning now to FIGS. 5-9, conventional bronchoscope 10 includes a viewing tube 90 having fiber optic bundles 92 which transmit light from a source (not shown) to the lungs of the patient, fiber optic bundle 94 which transmits the lung image to the operator, and hollow aspirating channel 96 which is conventionally used to suck mucus out of the field of view.

In use, tube 90 of bronchoscope 10 is passed through the nose, pharynx, and larynx of the patient and introduced into the airways of the lung. Tube 90 is maneuvered in the usual way until the lesion or questionable area of the lung is in direct view (FIG. 8).

The mucus suction source (not shown) is disconnected from aspirating channel 96. Holding grips 70 of clamp 16 and squeezing the grips to close levers 68 against aspirator 18 (FIGS. 3 and 4), the operator advances the assembled aspirating unit 12, with head 54 of obturator 24 locked securely in place in cavity 56 of adapter 20 (FIG. 2), through channel 96 into the lungs of the patient. (As best shown in FIG. 4, bushings 72 of levers 68 are adapted to clamp tube 40 of aspirator 18, but at the same time prevent inadvertent crushing of the aspirator.) The operator continually views the lungs through bronchoscope 10 while advancing catheter unit 12.

With tip 38 of catheter 30 of unit 12 in view, the spring loaded levers 68 are released, and aspirator 18 is slowly advanced within the catheter until needle 22 emerges from the tip of the catheter (FIG. 9) and penetrates the lesion or questionable area of the lung to the desired depth. The Teflon coating 34 inside tube 30 assures smooth, easily controlled sliding of aspirator 18 within tube 30. Obturator 24 is then withdrawn from catheter 18, and a syringe 98 is attached to adapter 20 (FIG. 5). A suction is applied to lumen 52 of needle 22 by means of syringe 98. Then, holding grips 70 and closing levers 68 against aspirator 18, the operator advances and retracts the aspirator several times, in turn advancing and retracting needle 22 within the lesion or questionable tissue to assure that an adequate sample of cell material is forced into lumen 52 of the needle. Needle guide 36 acts as a stop against hub 42 (FIG. 2) to prevent the needle from accidentally being advanced too far. Aspirator 18 is then withdrawn, and the retrieved cells are removed from the lumen of needle 22, placed on alcohol soaked slides, and prepared in the usual way for cytologic examination. The aspirator may be prepared and advanced through the bronchoscope for additional cell specimens, if necessary.

OTHER EMBODIMENTS

Other embodiments are within the following claims. For example, different tubing and needles could be used depending on the specific application of the unit; and the suction could be applied by means other than a syringe.

The unit has other important applications as well. For example, it could be adapted for use in connection with gastroenterology to examine the esophagus, stomach, and duodenum. There is a risk of rupturing blood vessels during biopsy of lesions in these areas with conventional equipment. Use of the present invention would tend to minimize this risk because the small caliber needle of the invention does not cause serious tears during penetration of the lesion. Similarly, the unit could be adapted for use in connection with a colonoscope to examine the rectum and colon, where tumors may contain many blood vessels.

Occasionally the blood vessels of the lower esophagus become greatly dilated due to liver disease, and the surgeon must know the pressure of the blood in those vessels. The unit could be adapted to be used for determining such pressure by filling aspirator 18 with a fluid, such as a saline solution, connecting adapter 20 to a manometer, and inserting needle 22 into the vessel to be tested.

What is claimed is:

1. A biopsy unit comprising:
an outer catheter, and
an inner aspirator disposed inside said catheter,
said catheter including
a longitudinally extending hollow flexible housing tube, and
means for selectively gripping said aspirator disposed near one end of said housing tube,
said aspirator including
a longitudinally extending hollow flexible aspirating tube disposed inside said housing tube and longitudinally slidable within said housing tube when not gripped by said gripping means,
a connector fastened to one end of said aspirating tube and adapted to be fitted to a suction source, and
a hollow needle fastened to the other end of said aspirating tube, said needle being less flexible than said aspirating tube, the lumen of said needle communicating with said connector through said aspirating tube,
whereby cell material is collected in the lumen of said needle when said aspirating tube is moved within said housing tube so that said needle is inserted into the cell material.

2. The biopsy unit of claim 1 further comprising:
an obturator having a longitudinally extending wire body slidingly fitting within said aspirating tube and the lumen of said needle.

3. The biopsy unit of claim 2 wherein said obturator further comprises:
a head attached to said wire body and being adapted to fit within said connector when said wire body is inserted in said aspirator.

4. The biopsy unit of claim 1 wherein said gripping means comprises:
a disc fastened to the proximal end of said housing tube, and
levers pivotally mounted to said disc,
said levers being adapted to clamp said aspirating tube.

5. The biopsy unit of claim 4 wherein,
said disc has an integral guide rib, and
each of said levers has a cooperating groove for movement along said guide rib.

6. The biopsy unit of claims 4 or 5 wherein said gripping means further comprises:
means for biasing said levers away from said aspirating tube,
said aspirating tube being normally unclamped by said levers.

7. The biopsy unit of claim 5 wherein,
each of said levers has a notch,
said notch of one lever being opposed to said notch of the other lever to define a cavity, and
said biasing means comprises a spring positioned within said cavity,
said spring biasing said levers away from each other.

8. The biopsy unit of claim 7 wherein,
said disc has stops to limit the movement of said levers under the biasing force of said spring.

9. The biopsy unit of claims 4 or 5 wherein,
said aspirating tube is cylindrical, and
each of said levers has a semicircular bushing adapted to clamp the periphery of said aspirating tube without crushing said aspirating tube.

10. The biopsy unit of claim 1 wherein,
said housing tube and said aspirating tube are polyethylene.

11. The biopsy unit of claim 10 wherein,
the walls of said housing tube are coated with Teflon.

12. The biopsy unit of claim 1 wherein,
said housing tube has an outside diameter no greater than 1.5 mm.

13. The biopsy unit of claim 1 wherein,
said needle is a stainless steel needle no greater than 22 gauge.

14. The biopsy unit of claim 1 wherein,
said connector includes means for fitting a syringe.

15. The biopsy unit of claim 1 wherein,
said connector includes means for fitting a manometer.

16. The biopsy unit of claim 1 wherein,
said housing tube has an integral stop to limit the longitudinal movement of said needle of said aspirator.

* * * * *